United States Patent
Lee (10) Patent No.: US 6,235,226 B1
(45) Date of Patent: May 22, 2001

(54) METHOD FOR MANUFACTURING BALLOON CATHETER

(76) Inventor: Keun Ho Lee, #802, Lotte Apt. 1-dong, 617-11, Simgok-Bon-dong, Sosa-gu, Bucheon City, Kyungki-do (KR)

( * ) Notice: Subject to any disclaimer, the term of this patent is extended or adjusted under 35 U.S.C. 154(b) by 0 days.

(21) Appl. No.: 09/357,495

(22) Filed: Jul. 20, 1999

(51) Int. Cl.[7] .................................................. B29C 63/00
(52) U.S. Cl. ........................ 264/130; 264/134; 264/139; 264/250; 264/279; 264/317; 427/2.3; 427/300; 427/443
(58) Field of Search .................................. 264/130, 139, 264/134, 250, 279, 271.1, 344, 221, 317, 275; 427/2.3, 300, 443

(56) References Cited

U.S. PATENT DOCUMENTS

| | | | |
|---|---|---|---|
| 5,137,671 | * 8/1992 | Conway et al. | 264/130 |
| 5,484,565 | * 1/1996 | Larsen et al. | 264/230 |
| 5,571,567 | * 11/1996 | Shah | 427/379 |
| 5,811,043 | * 9/1998 | Horrigan et al. | 264/138 |

* cited by examiner

*Primary Examiner*—Jan H. Silbaugh
*Assistant Examiner*—Edmund H. Lee
(74) *Attorney, Agent, or Firm*—Lee & Hong

(57) ABSTRACT

Disclosed is a method for manufacturing a balloon catheter. The method comprises the steps of: preparing a tube which is formed with a first lumen and a second lumen, the tube possessing a balloon expansion section in which a first hole for communicating an inside of the first lumen with an outside of the balloon catheter is defined; filling polymeric filler material into a part of the first lumen which extends from one end of the first lumen to a point where the first hole is defined, and attaching a tip member to one end of the tube; fitting a cap member around the tube except the balloon expansion section, and dipping the tube into releasing agent solution and solidifying the releasing agent solution, such that an outer surface of the balloon expansion section is coated with releasing agent and the first hole and another part of the first lumen which extends from the point where the first hole is defined to the other end of the balloon expansion section, are filled with releasing agent; removing the cap member from the resultant tube and dipping the tube into liquid silicone to form an over-coating layer onto an entire outer surface of the tube; and removing the releasing agent which is coated onto the outer surface of the balloon expansion section and filled into the first hole and the another part of the first lumen.

1 Claim, 8 Drawing Sheets

METHOD FOR MANUFACTURING BALLOON CATHETER

BACKGROUND OF THE INVENTION

1. Field of the Invention

The present invention relates to a method for manufacturing a balloon catheter, and more particularly, the present invention relates to a method for manufacturing a balloon catheter which is, as a medical appliance, fitted into a tube-shaped organ of the body and a portion of which is maintained in an expanded state to allow liquid medicine to be injected therein and liquid excrement to be removed therefrom.

2. Description of the Related Art

Generally, a balloon catheter is made of silicone to be medically superior. A method for manufacturing a balloon catheter will be described hereinafter with reference to U.S. Pat. No. 5,137,671.

Figure 1:
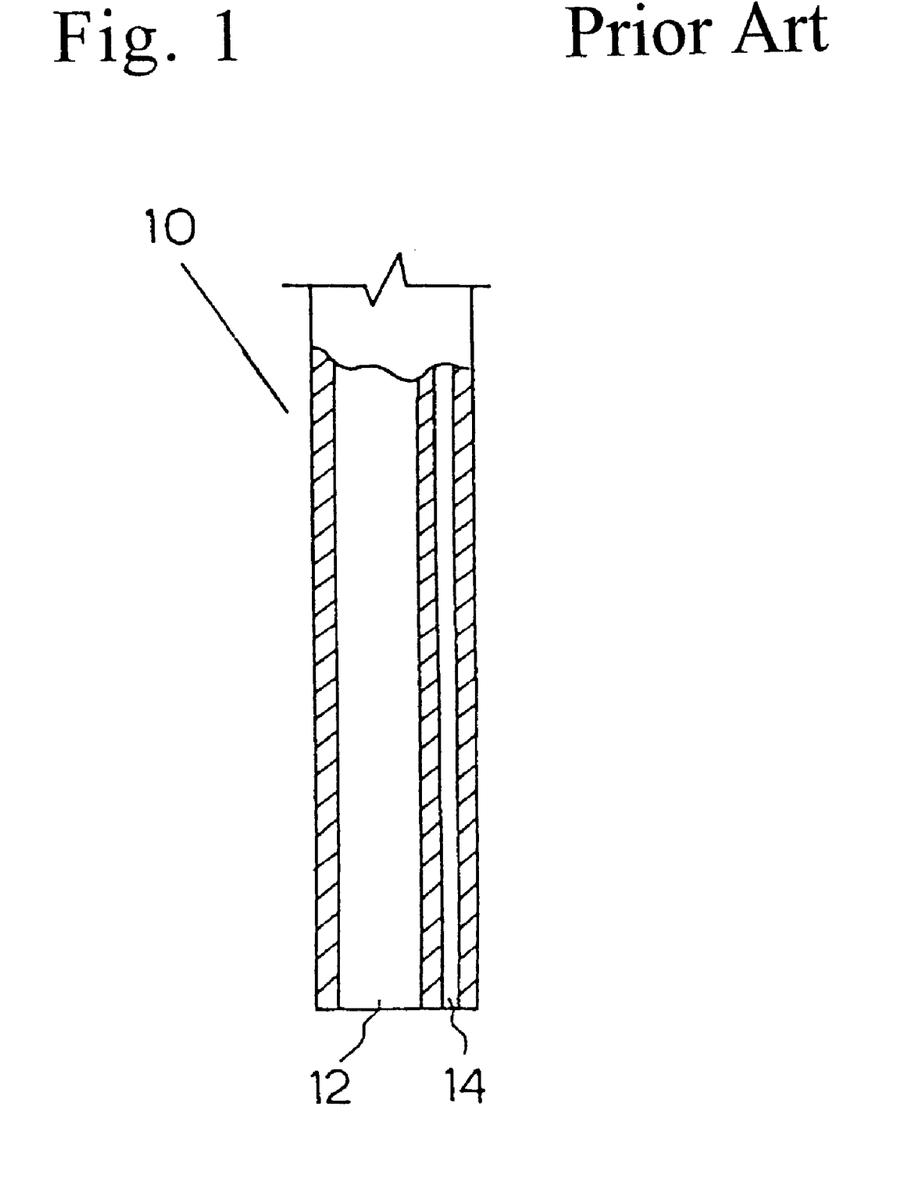
FIGS. 1 through 6 are longitudinal cross-sectional views sequentially illustrating processes for manufacturing a balloon catheter of the conventional art.

Referring to the drawings, a tube 10 as shown in FIG. 1 is provided. The tube 10 is formed with a first lumen 14 (a capillary tube of a smaller diameter) and a second lumen 12 (a tube of a larger diameter).

Figure 2:
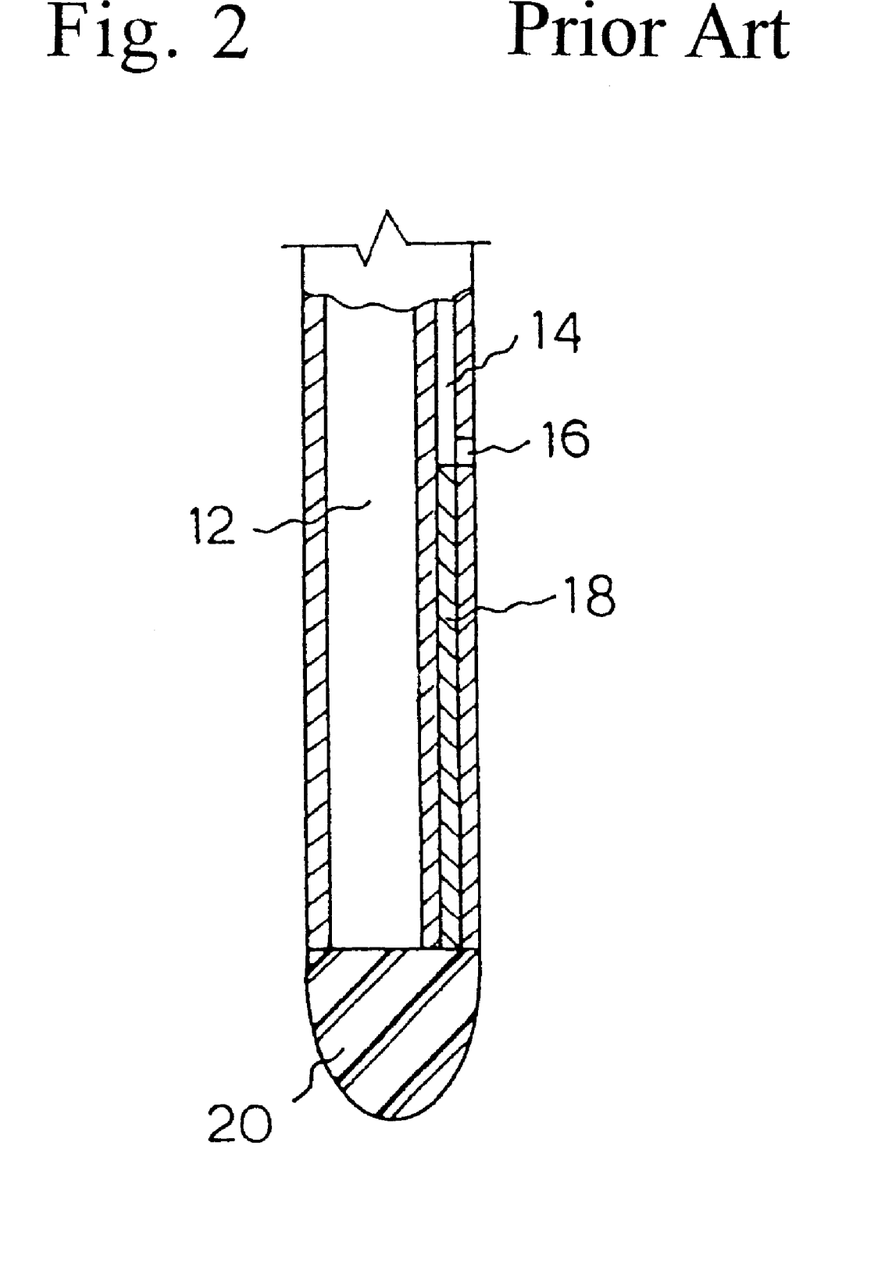

In a state that the tube 10 as described above is prepared, a middle portion of the tube 10, that is, a balloon expansion section of the tube 10 is, as shown in FIG. 2, formed with a first hole 16 which communicates an inside of the first lumen 14 with an outside of the tube 10. Then, polymeric filler material 18 such as silicone rubber is filled into a part of the first lumen 14 which extends from a lower end of the first lumen 14 to a point where the first hole 16 is defined, and a tip member 20 is attached to a lower end of the tube 10 from which the polymeric filler material 18 is filled into the first lumen 14, whereby lower ends of the first and second lumens 14 and 12 are closed.

Figure 3:
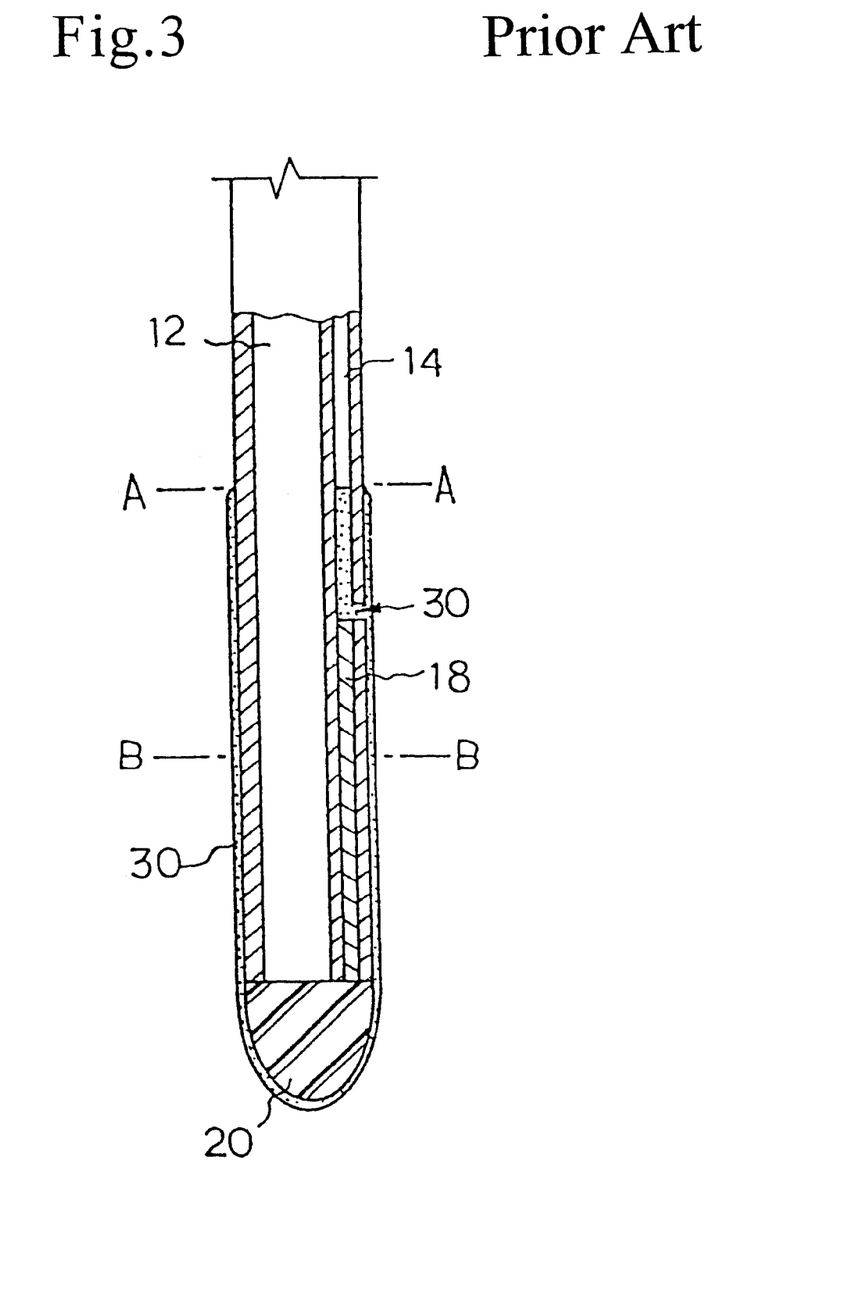

Thereafter, a part of the tube 10 which extends from the lower end thereof and to an upper end of the balloon expansion section as shown by the line A—A in FIG. 3, is dipped into releasing agent solution (such as soapy water, Vaseline solution or the like), and the releasing agent solution is solidified to leave releasing agent 30 onto the part of the tube 10. At this time, releasing agent 30 is filled into the first hole 16 and another part of the first lumen 14 which extends from the point where the first hole 16 is defined to the upper end of the balloon expansion section as shown by the line A—A in FIG. 3. Consequently, the tube 10 has a cross-section as shown in FIG. 3. That is to say, the releasing agent 30 is filled into the first lumen 14 from the upper end of the balloon expansion section as shown by the line A—A in FIG. 3 to the first hole 16, and is coated onto an outer surface of the tube 10 between the upper end of the balloon expansion section as shown by the line A—A in FIG. 3 and the end of the tip member 20 as shown in FIG. 3.

Then, as shown in FIG. 4, another part of the tube 10 which extends from the lower end thereof to the lower end of the balloon expansion section as shown by the line B—B in FIG. 4 is dipped again into water or hot liquid, to remove the releasing agent coated onto the outer surface of the tube 10 except the balloon expansion section, and a first over-coating layer 41 and a second over-coating layer 42 are sequentially coated onto an entire outer surface of the tube 10, to define an over-coating layer 40.

Figure 6:
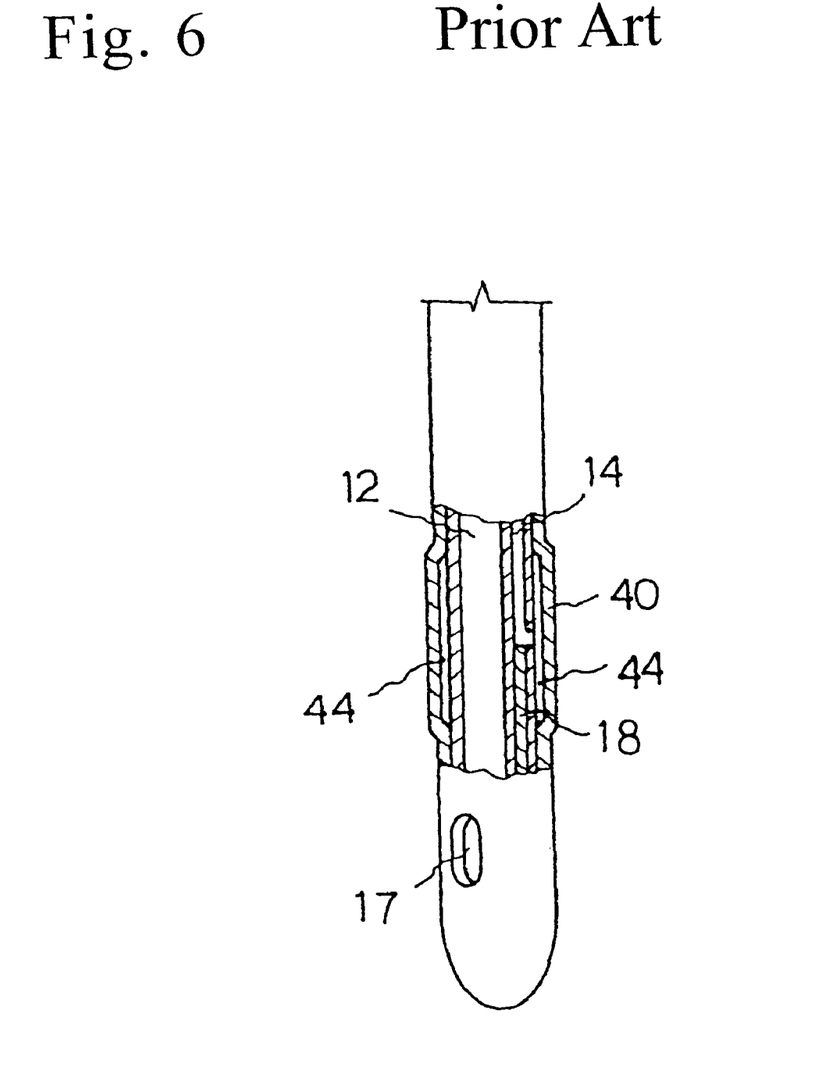
Figure 7:
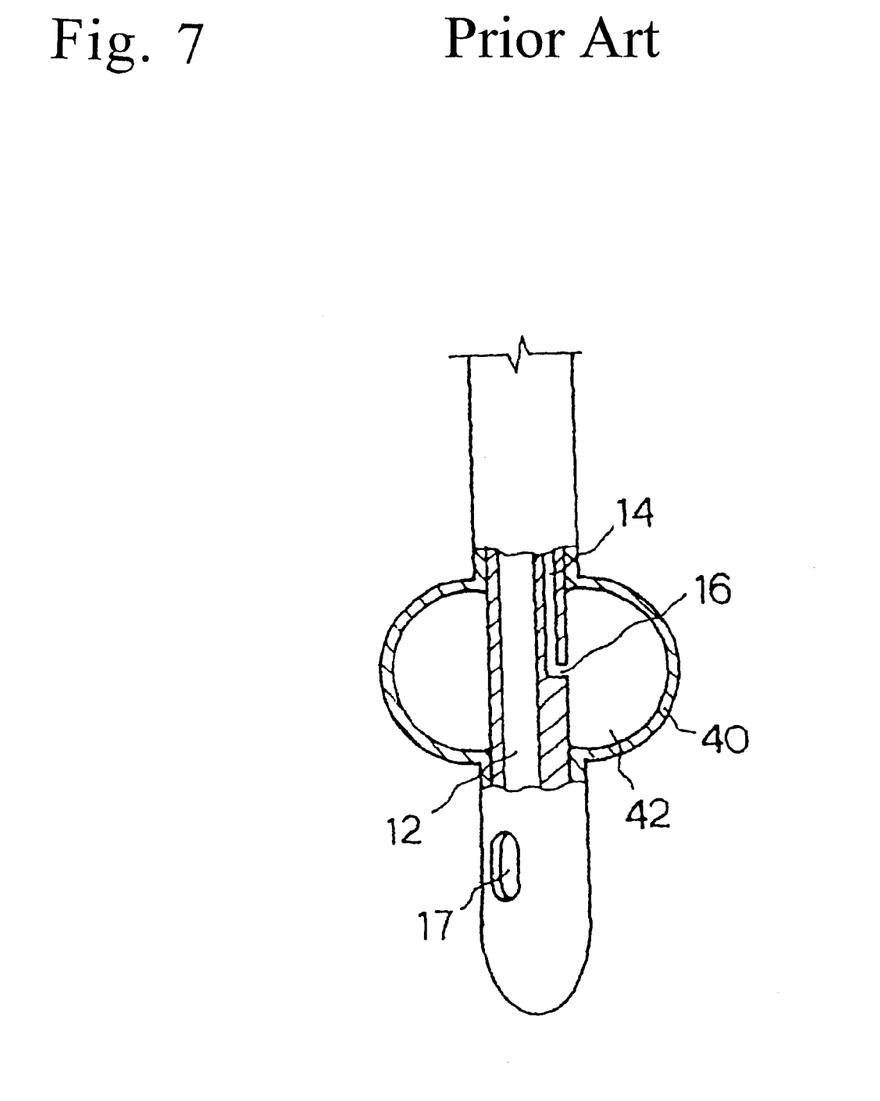
FIG. 7 is a partially broken-away front view illustrating a balloon expansion section of the conventional balloon catheter.

Then, the releasing agent which is filled into the first lumen 14 and the first hole 16 and coated onto the outer surface of the balloon expansion section, is removed through the first lumen 14, thereby defining a space part 44 as shown in FIG. 6 for allowing the balloon expansion section to be expanded.

However, when a balloon catheter is manufactured by the processes of the conventional art, as described above, an amount of waste water which is generated when removing the releasing agent coated onto the outer surface of the tube 10 except the balloon expansion section after dipping the tube 10 into releasing agent solution, is increased in the course of dipping the tube 10 into water, etc. through a number of times, thereby causing environmental pollution.

Further, in the case that the releasing agent is not perfectly removed, when the balloon expansion section is expanded after the space part is formed, a portion of the over-coating layer adjoining the balloon expansion section is peeled off, thereby to be expanded together with the balloon expansion section.

SUMMARY OF THE INVENTION

Accordingly, the present invention has been made in an effort to solve the problems occurring in the related art, and an object of the present invention is to provide a method for manufacturing a balloon catheter which can actively cope with a problem of environmental pollution caused in the process of coating and removing releasing agent and eliminate a phenomenon that a portion of an over-coating layer adjoining a balloon expansion section is peeled off, thereby preventing the portion of the over-coating layer from being expanded together with the balloon expansion section.

In order to achieve the above object, according to one aspect of the present invention, there is provided a method for manufacturing a balloon catheter, the method comprising the steps of: a first step of preparing a tube which is formed with a plurality of lumens including at least a first lumen and a second lumen, the tube possessing a balloon expansion section in which a first hole for communicating an inside of the first lumen with an outside of the balloon catheter is defined; a second step of filling polymeric filler material into a part of the first lumen which extends from one end of the first lumen to a point where the first hole is defined, and attaching a tip member to one end of the tube from which the polymeric filler material is filled; a third step of fitting a cap member around the one end of the tube to which the tip member is attached except at least the balloon expansion section in which the first hole is defined, and dipping the tube into releasing agent solution and solidifying the releasing agent solution, such that an outer surface of the balloon expansion section of the tube is coated with releasing agent and such that the first hole and another part of the first lumen which extends from the point where the first hole is defined to the other end of the balloon expansion section, are filled with releasing agent; a fourth step of dipping the resultant tube obtained from the third step into liquid silicone to form an over-coating layer onto an entire outer surface of the tube; and a fifth step of removing through the first lumen the releasing agent which is coated onto the outer surface of the balloon expansion section and filled into the first hole and the another part of the first lumen.

By the features of the present invention, due to the fact that a cap member is used upon coating releasing agent, since the releasing agent is not coated onto a portion of a tube except a balloon expansion section, a problem of environmental pollution caused when removing an unnecessary portion of the releasing agent in the conventional art is solved, and it is possible to prevent a portion of an over-coating layer adjoining the balloon expansion section from being expanded along with the balloon expansion section when water is poured into the balloon expansion section.

BRIEF DESCRIPTION OF THE DRAWINGS

The above objects, and other features and advantages of the present invention will become more apparent after a reading of the following detailed description when taken in conjunction with the drawings, in which.

DETAILED DESCRIPTION OF PREFERRED EMBODIMENTS

Reference will now be made in greater detail to a preferred embodiment of the invention, an example of which is illustrated in the accompanying drawings. Wherever possible, the same reference numerals will be used throughout the drawings and the description to refer to the same or like parts.

First, as shown in FIGS. 1 and 2, a tube 10 which is formed with a first lumen 14 and a second lumen 12, is provided, and a middle portion of the tube 10, that is, a balloon expansion section of the tube 10 is formed with a first hole 16 which communicates an inside of the first lumen 14 with an outside of the tube 10. Then, polymeric filler material 18 such as silicone rubber is filled into a part of the first lumen 14 which extends from a lower end of the first lumen 14 to a point where the first hole 16 is defined, and a tip member 20 is attached to a lower end of the tube 10 from which the polymeric filler material 18 is filled into the first lumen 14, whereby lower ends of the first and second lumens 14 and 12 are closed.

Figure 4:
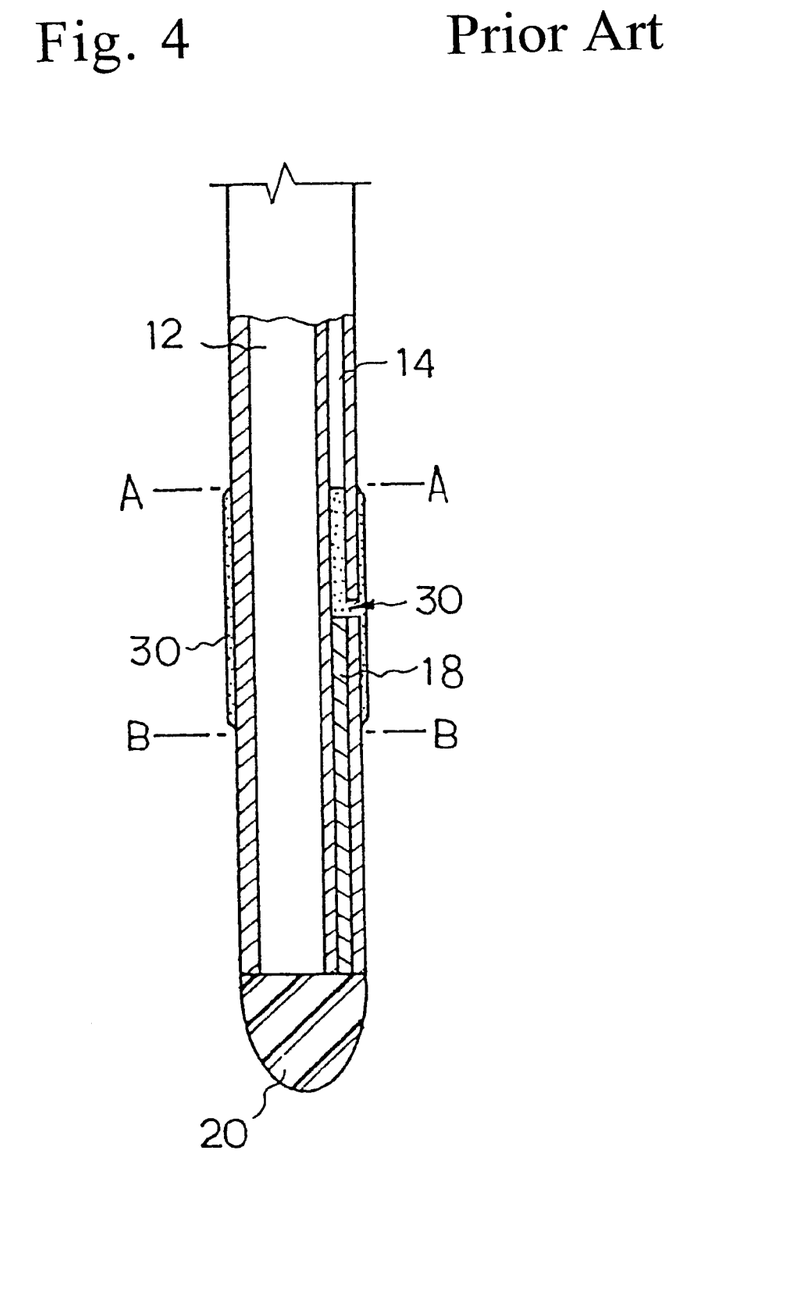
Figure 8:
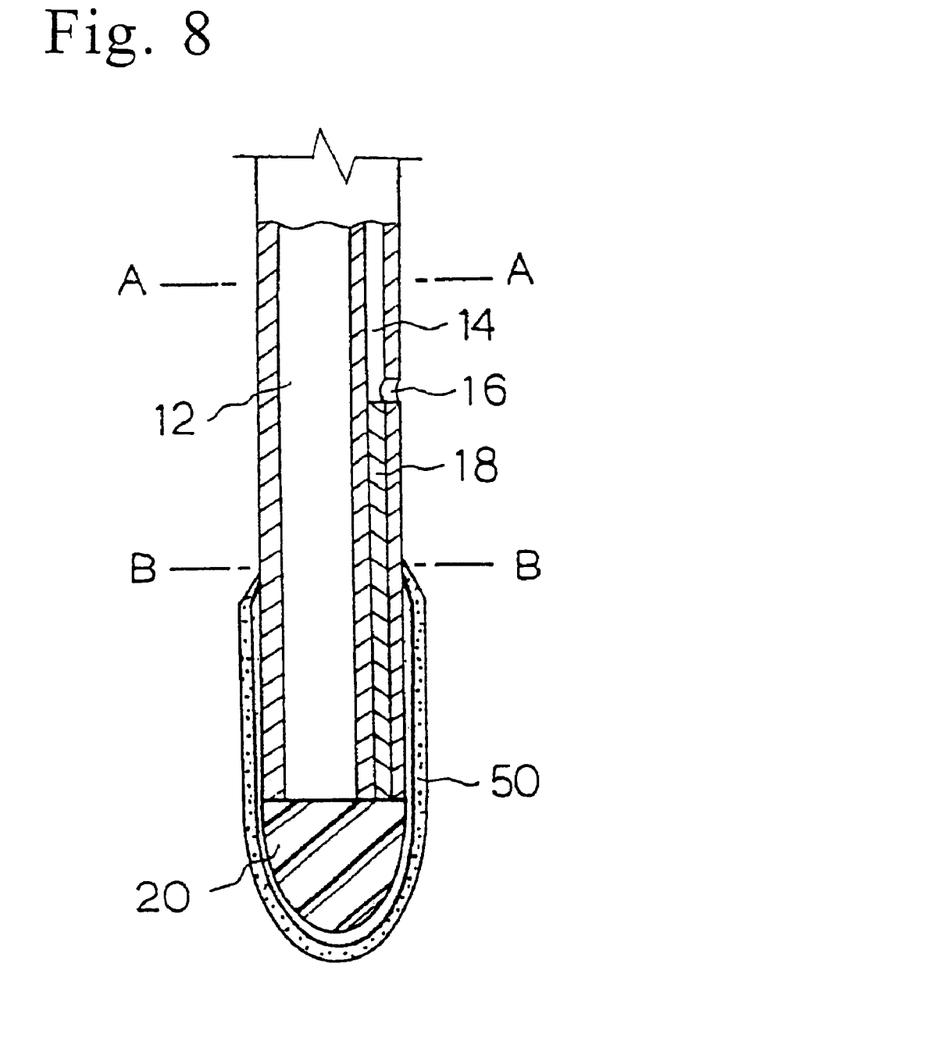
FIG. 8 is a longitudinal cross-sectional view illustrating a process of a method for manufacturing a balloon catheter in accordance with an embodiment of the present invention.

Thereafter, as being characterizing features of the present invention, processes for coating and removing releasing agent are performed. To be more detailed, as shown in FIG. 8, a cap member 50 is fitted around a part of the tube 10 which extends from the end of the tip member 20 attached to the lower end of the tube 10 to a lower end of the balloon expansion section as shown by the line B—B in FIG. 8, and thereafter, the tube 10 is dipped into releasing agent solution to an upper end of the balloon expansion section as shown by the line A—A in FIG. 8. Then, after the releasing agent solution is solidified, the cap member 50 is removed. After performing the above processes, the tube 10 has the cross-section as shown in FIG. 4.

In the above dipping process into the releasing agent, although the cap member 50 is fitted around the tube 10 only over a lower portion thereof, it is to be readily understood that another cap member can be fitted around an upper portion of the tube 10 downward to the upper end of the balloon expansion section as shown by the line A—A in FIG. 8.

In this case, while it is possible to dip the entire tube 10 into the soapy water, it is not preferred in view of environmental pollution.

Here, the cap member 50 is made of metal or synthetic resin. In an example in which the tube 10 is dipped into the releasing agent solution, the tube 10 is dipped into soapy water having a low concentration, at a temperature of 40–50° C. At this time, Vaseline solution can be used as the releasing agent solution.

Then, the tube 10 is taken out from the releasing agent solution, and is dried using air of a temperature of 50° C., to solidify the releasing agent solution.

In the above process, since the releasing agent is only coated onto an outer surface of the balloon expansion section of the tube 10 and is only filled into the first hole 16 and the first lumen 14, a process for removing an unnecessary portion of releasing agent in the conventional art is not needed. Also, due to the fact that only a small amount of releasing agent is removed when defining a space part for allowing the balloon expansion section to be expanded, the balloon catheter is more advantageous than the conventional art from the viewpoint of environmental pollution.

Moreover, because the releasing agent is brought into contact only with the balloon expansion section, an over-coating layer 40 which defines the space part for allowing the balloon expansion section to be expanded can come into close contact with the outer surface of the tube 10, whereby a phenomenon that a portion of the over-coating layer adjoining the balloon expansion section is peeled off when water is poured into the space part thereby to be expanded together with the balloon expansion section, is prevented from occurring.

Figure 5:
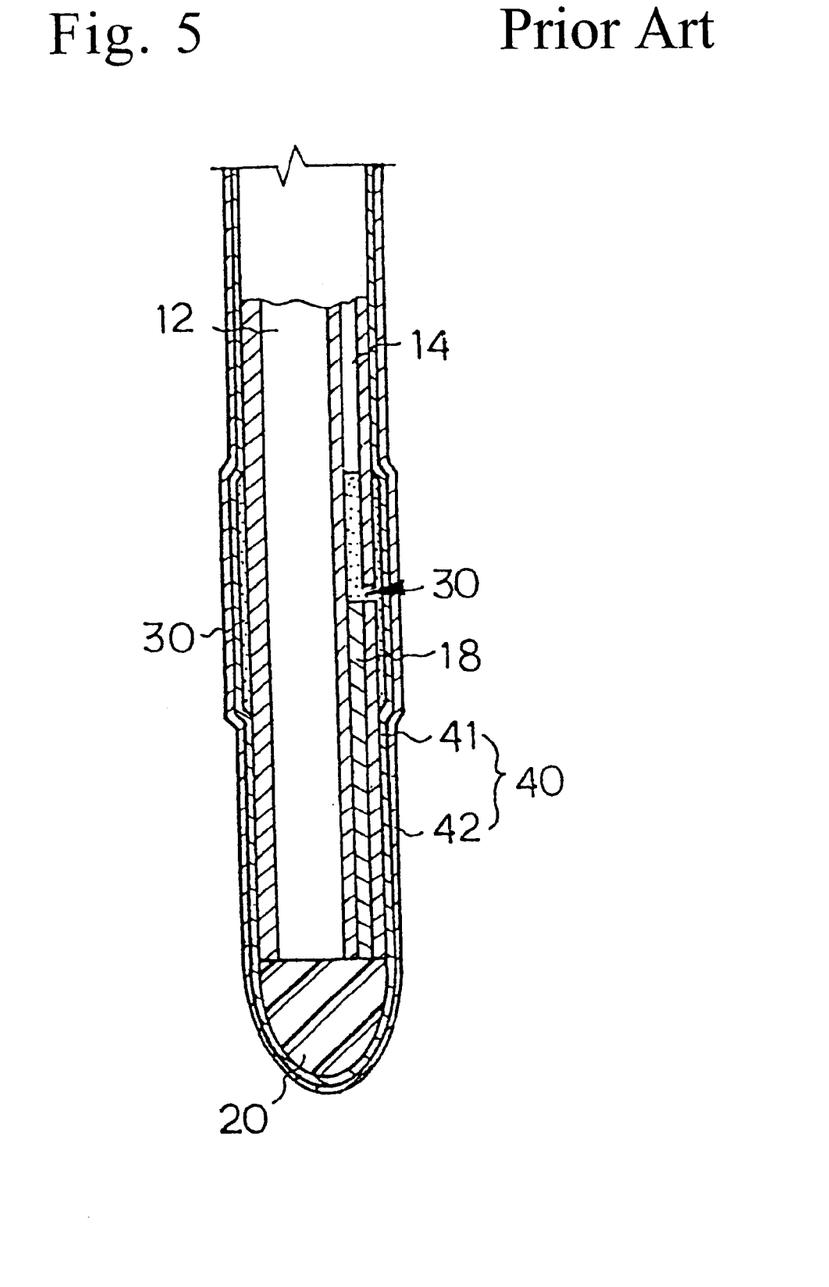

Next processes are implemented in the same way as in the conventional art. In other words, as shown in FIG. 5, a first over-coating layer 41 and a second over-coating layer 42 are sequentially coated onto the entire outer surface of the tube 10, to define the over-coating layer 40. Then, the releasing agent which is filled into the first lumen 14 and the first hole 16 and coated onto the outer surface of the balloon expansion section, is removed through the first lumen 14, thereby defining the space part 44 as shown in FIG. 6 to allow the balloon expansion section to be expanded. Also, by perforating a second hole which is communicated with an inside of the second lumen 12, through the over-coating layer 40 at the lower end of the tube 10 adjacent the tip 20, the balloon catheter according to the present invention is completed.

As described above, by manufacturing a balloon catheter by the method according to the present invention, advantages are provided in that since a portion of a tube except a balloon expansion section is not brought into contact with releasing agent when the releasing agent is coated on the balloon expansion section, a process for removing an unnecessary portion of the releasing agent can be eliminated in the conventional art, whereby the number of manufacturing processes is decreased and environmental pollution is prevented. Further, it is possible to prevent a portion of an over-coating layer adjoining the balloon expansion section from being peeled off therefrom when water is poured into a space part defined in the balloon expansion section due to the fact that the releasing agent remains on the portion of the tube except the balloon expansion section. Moreover, if a cap member is precisely fitted around the tube when dipping the tube into releasing agent solution, next processes can be manually performed in an easy manner.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A method for manufacturing a balloon catheter, the method comprising the steps of:

a first step of preparing a tube which is formed with a plurality of lumens including at least a first lumen and a second lumen, the tube possessing a balloon expansion section in which a first hole for communicating an inside of the first lumen with an outside of the balloon catheter is defined;

a second step of filling polymeric filler material into a part of the first lumen which extends from one end of the first lumen to a point where the first hole is defined, and attaching a tip member to one end of the tube from which the polymeric filler material is filled;

a third step of fitting a cap member around the tube except at least the balloon expansion section in which the first hole is defined, and dipping the tube into releasing agent solution and solidifying the releasing agent solution, such that an outer surface of the balloon expansion section of the tube is coated with releasing agent and such that the first hole and another part of the first lumen which extends from the point where the first hole is defined to the other end of the balloon expansion section, are filled with releasing agent;

a fourth step of removing the cap member from the resultant tube obtained from the third step and dipping the tube into liquid silicone to form an over-coating layer onto an entire outer surface of the tube; and a fifth step of removing through the first lumen the releasing agent which is coated onto the outer surface of the balloon expansion section and filled into the first hole and the another part of the first lumen.

* * * * *